(12) United States Patent
Molloy et al.

(10) Patent No.: US 10,726,688 B2
(45) Date of Patent: *Jul. 28, 2020

(54) FACILITATING A SEARCH OF INDIVIDUALS IN A BUILDING DURING AN EMERGENCY EVENT

(71) Applicant: INTERNATIONAL BUSINESS MACHINES CORPORATION, Armonk, NY (US)

(72) Inventors: Christopher L. Molloy, Raleigh, NC (US); Bernadette A. Pierson, South Hero, VT (US); Jayashree Vaidyanathan, Cincinnati, OH (US); Edgar A. Zamora Duran, Santo Domingo (CR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/540,515

(22) Filed: Aug. 14, 2019

(65) Prior Publication Data

US 2019/0371138 A1 Dec. 5, 2019

Related U.S. Application Data

(63) Continuation of application No. 15/627,971, filed on Jun. 20, 2017.

(51) Int. Cl.
*G01C 21/20* (2006.01)
*G01C 21/26* (2006.01)
(Continued)

(52) U.S. Cl.
CPC ............ *G08B 7/066* (2013.01); *A61B 5/0205* (2013.01); *A61B 5/0295* (2013.01);
(Continued)

(58) Field of Classification Search
CPC .... G01C 21/206; G01C 21/26; G06N 99/005; G06N 20/00; G06N 3/006; G06N 3/0445;
(Continued)

(56) References Cited

U.S. PATENT DOCUMENTS 6,505,203 B1    1/2003  Adler
2004/0212630 A1  10/2004  Hobgood et al.
(Continued)

OTHER PUBLICATIONS

Mell et al., "The NIST Definition of Cloud Computing", NIST, Special Publication 800-145, Sep. 2011, 7 pages.
(Continued)

*Primary Examiner* — Dionne Pendleton
(74) *Attorney, Agent, or Firm* — Jay Wahlquist; Andrew D. Wright; Roberts Calderon Safran & Cole, P.C.

(57) ABSTRACT

A computer-implemented method includes: determining, by a computing device, a location of an individual in a building relative to the location of an exit of the building; determining, by the computing device, the location of obstacles or hazards within the building; determining, by the computing device, a path from the individual to the exit based on determining the location of the individual relative to the exit and the location of the obstacles or hazards; generating, by the computing device, signaling instructions based on the path; and outputting, by the computing device, the signaling instructions to one or more signaling devices, wherein the outputting the signaling instructions control operations of the one or more signaling devices to guide the individual to the exit based on the path.

20 Claims, 10 Drawing Sheets

(51) Int. Cl.

| | |
|---|---|
| *G08B 7/06* | (2006.01) |
| *G01C 21/34* | (2006.01) |
| *G06F 3/0481* | (2013.01) |
| *G06F 1/16* | (2006.01) |
| *A62B 3/00* | (2006.01) |
| *A62B 5/00* | (2006.01) |
| *H04W 52/02* | (2009.01) |
| *G08B 25/01* | (2006.01) |
| *G08B 21/02* | (2006.01) |
| *H04W 4/90* | (2018.01) |
| *G08B 27/00* | (2006.01) |
| *H04W 4/33* | (2018.01) |
| *A61B 5/0402* | (2006.01) |
| *A61B 5/0205* | (2006.01) |
| *A61B 5/0295* | (2006.01) |
| *G06F 3/0484* | (2013.01) |
| *H04W 4/02* | (2018.01) |

(52) U.S. Cl.
CPC ............ *A61B 5/0402* (2013.01); *A62B 3/005* (2013.01); *A62B 5/00* (2013.01); *G01C 21/20* (2013.01); *G01C 21/206* (2013.01); *G01C 21/26* (2013.01); *G01C 21/34* (2013.01); *G01C 21/3461* (2013.01); *G06F 1/163* (2013.01); *G06F 3/0481* (2013.01); *G06F 3/0484* (2013.01); *G08B 21/02* (2013.01); *G08B 21/0272* (2013.01); *G08B 25/016* (2013.01); *G08B 27/001* (2013.01); *H04W 4/33* (2018.02); *H04W 4/90* (2018.02); *H04W 52/0254* (2013.01); *H04W 52/0261* (2013.01); *H04W 4/02* (2013.01)

(58) Field of Classification Search
CPC ...... G08B 17/10; G08B 17/113; G08B 21/10; G08B 25/10; G08B 29/14; G08B 29/188; G08B 29/24; G08B 25/016; G08B 21/02; G08B 21/0423; G08B 21/0446; G08B 21/0453; G08B 21/0461; G08B 21/0476; G08B 21/0484; G08B 21/0492; H04W 4/22; H04W 4/90; H04W 84/18; H04W 52/0254; H04W 52/0261; G06F 1/163; G06F 3/0481; G06F 19/00; G06F 199/3418; G06F 19/3462; G06F 3/011; G06F 3/012; G06F 3/0482; G06F 3/0484; G06F 3/04842; G16H 15/00; G16H 20/13; G16H 40/67; G16H 50/20; G16H 80/00; H04M 19/04; H04M 2250/12; H04M 3/5116; G06Q 50/265; A61B 2562/0219; A61B 5/0006; A61B 5/0008; A61B 5/0013; A61B 5/002; A61B 5/0022; A61B 5/0077; A61B 5/01; A61B 5/0205; A61B 5/02416; A61B 5/02055; A61B 5/0261; A61B 5/0402; A61B 5/0476; A61B 5/0488; A61B 5/053; A61B 5/1112; A61B 5/1116; A61B 5/1117; A61B 5/1118; A61B 5/14551; A61B 5/6803; A61B 5/6806; A61B 5/6807; A61B 5/681; A61B 5/6824; A61B 5/6826; A61B 5/6891; A61B 5/7264; A61B 5/7445; A61B 7/04; A61B 7/045; A61B 8/00; A61B 8/06; A61B 8/0808; A61B 8/488; A61B 5/565; A61B 2090/064; A61B 2560/0209; A61B 2560/0252; A61B 2560/0257; A61B 2560/0456; A61B 2560/0475; A61B 2562/0223; A61B 2562/0261; A61B 5/4875; A61B 5/7221; A62B 5/00; G02B 27/01; G02B 27/017; G06T 17/20; G06T 2215/16; G09G 2340/0492; G09G 2340/14; G09G 3/001; G09G 5/00; G09G 5/36

See application file for complete search history.

(56) References Cited

U.S. PATENT DOCUMENTS

| | | |
|---|---|---|
| 2009/0018875 A1 | 1/2009 | Monatesti et al. |
| 2011/0169634 A1* | 7/2011 | Raj ................. G08B 27/008 340/540 |
| 2012/0092157 A1 | 4/2012 | Tran |
| 2014/0236483 A1* | 8/2014 | Beaurepaire ....... G01C 21/3626 701/533 |
| 2014/0278388 A1* | 9/2014 | Watson ................ G10L 25/63 704/231 |
| 2014/0329491 A1 | 11/2014 | Scott |
| 2015/0048932 A1 | 2/2015 | Helms |
| 2015/0338728 A1* | 11/2015 | Amron ............... G03B 21/2053 33/228 |
| 2016/0034479 A1 | 2/2016 | Skocic |
| 2016/0284038 A1 | 9/2016 | Johnson |
| 2017/0067747 A1* | 3/2017 | Ricci ................... B60R 25/00 |
| 2017/0176190 A1 | 6/2017 | Harvey |
| 2017/0329480 A1 | 11/2017 | Ishikawa et al. |
| 2018/0040230 A1 | 2/2018 | Benoit et al. |
| 2018/0365942 A1* | 12/2018 | Molloy ............... G06F 3/0481 |
| 2019/0069245 A1 | 2/2019 | Miller et al. |

OTHER PUBLICATIONS

List of IBM Patents or Patent Applications Treated as Related, dated Aug. 14, 2019, 1 page.

* cited by examiner

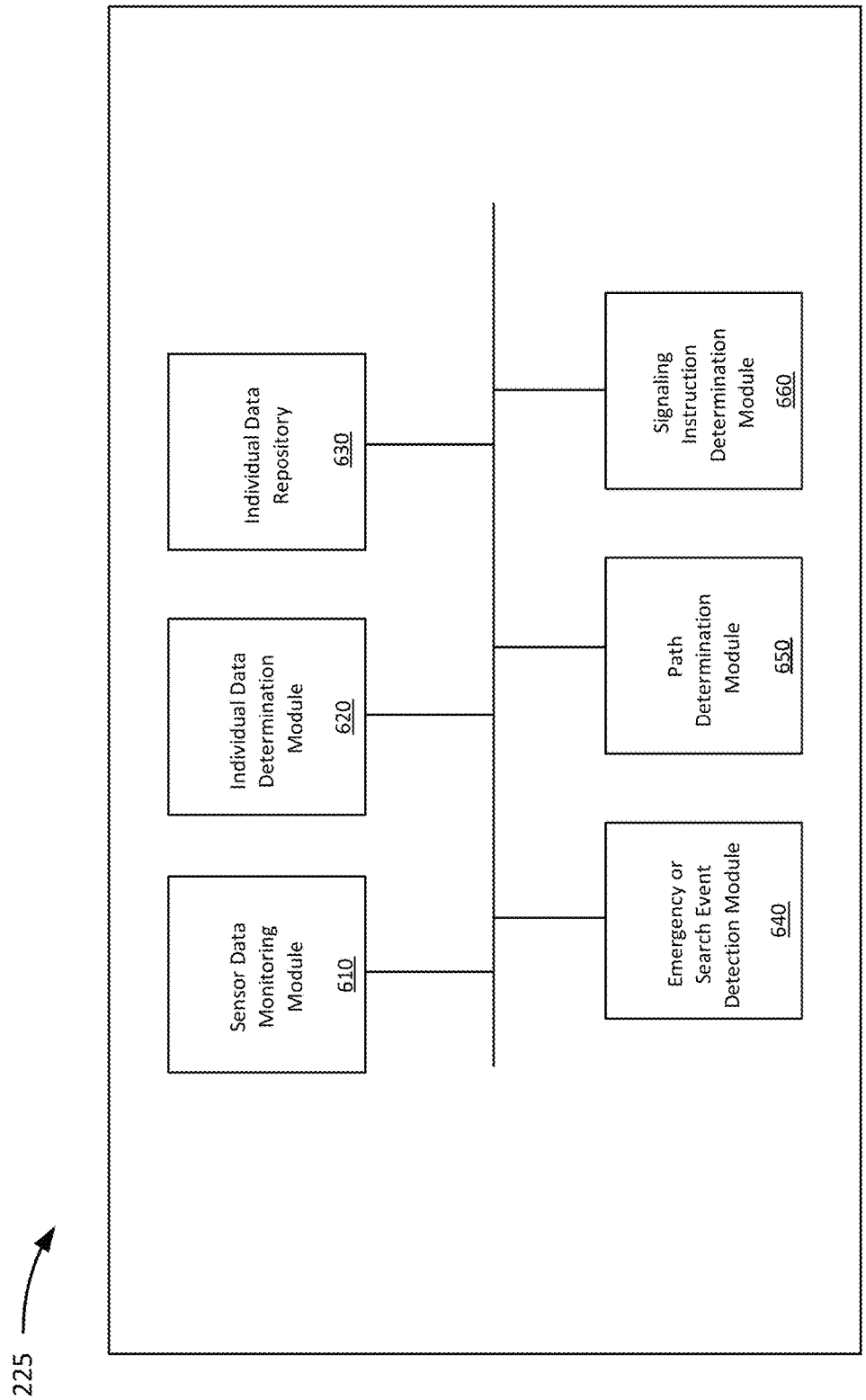

| Individual Name | Individual Location | Known Health Data | Real-time Health Data | Sensor Information | Status/Injury Score | User Device Information | Location of Nearest Responder | Location of Nearest Exit | Path to Exit | Path to Responder | Signaling Devices for Guidance |
|---|---|---|---|---|---|---|---|---|---|---|---|
| Jon Doe | Room 404 | Heart condition | Heart rate = 90 bpm Blood pressure = | Sensor Data Set 1 | Conscious; Moderate Risk | Device ID 1 IMEI 1 | 4th floor break room 1 | Ground floor east side corridoor | Travel South 15 feet-->Travel | Travel South 10 feet-->Travel east 13 feet | Light group 1, speaker group 1, electronic |
| Jane Doe | Conference room 6 | None | Heart rate | Sensor Data Set 2 | Conscious; Low Risk | Device ID 2 IMEI 2 | 5th floor foyer | Ground floor west side corridoor | Travel North 15 feet-->Travel | Travel west 10 feet-->Travel south 13 feet | Light group 2, speaker group 2, electronic |
| Unknown | Bathroom 3 | Unknown | Unknown | Sensor Data Set 3 | Unconscious; Severe Risk | N/A | 2nd floor east hallway | Ground floor south side corridoor | Travel East 15 feet-->Travel south 10 | Travel west 10 feet-->Travel north 13 feet | Light group 3, speaker group 3, electronic |

FACILITATING A SEARCH OF INDIVIDUALS IN A BUILDING DURING AN EMERGENCY EVENT

BACKGROUND

The present invention generally relates to facilitating the search of individuals in a building and, more particularly, to facilitating the search of individuals in a building by controlling the operation of signaling devices to aid in the evacuation of individuals in the building during an emergency event.

During a building emergency event (e.g., a fire, flood, and/or other event requiring evacuation of the building), rescue response teams may be dispatched to assist with evacuating individuals located within the building. Situations may arise in which locating individuals may be difficult if the individual is incapacitated or otherwise unable to be found.

SUMMARY

In an aspect of the invention, a computer-implemented method includes: determining, by a computing device, a location of an individual in a building relative to the location of an exit of the building; determining, by the computing device, the location of obstacles or hazards within the building; determining, by the computing device, a path from the individual to the exit based on determining the location of the individual relative to the exit and the location of the obstacles or hazards; generating, by the computing device, signaling instructions based on the path; and outputting, by the computing device, the signaling instructions to one or more signaling devices, wherein the outputting the signaling instructions control operations of the one or more signaling devices to guide the individual to the exit based on the path.

In an aspect of the invention, there is a computer program product for assisting with rescue operations during a building emergency. The computer program product includes a computer readable storage medium having program instructions embodied therewith, the program instructions executable by a computing device to cause the computing device to: determine a location of an individual in a building relative to the location of a responder; determine the location of obstacles or hazards within the building; determine a path from the individual to the responder based on determining the location of the individual relative to the responder and the location of the obstacles or hazards; generate signaling instructions based on the path; and output the signaling instructions to one or more signaling devices, wherein the outputting the signaling instructions control operations of the one or more signaling devices to guide the individual to the responder or the responder to the individual based on the path.

In an aspect of the invention, a system includes: a CPU, a computer readable memory and a computer readable storage medium associated with a computing device; program instructions to determine a location of an individual in a building relative to the location of a responder or relative to a location of an exit of the building; program instructions to determine the location of obstacles or hazards within the building; program instructions to determine a path from the individual to the responder or a path from the individual to the exit based on determining the location of the individual and the location of the obstacles or hazards; program instructions to generate signaling instructions based on the path; and program instructions to output the signaling instructions to one or more signaling devices, wherein the outputting the signaling instructions control operations of the one or more signaling devices to guide the individual to the responder, the responder to the individual, or the individual to the exit based on the path. The program instructions are stored on the computer readable storage medium for execution by the CPU via the computer readable memory.

BRIEF DESCRIPTION OF THE DRAWINGS

The present invention is described in the detailed description which follows, in reference to the noted plurality of drawings by way of non-limiting examples of exemplary embodiments of the present invention.

FIG. 6 shows a block diagram of example components of a search assistance server in accordance with aspects of the present invention.

FIG. 7 shows an example data structure of data stored by the search assistance server for generating signaling instructions in accordance with aspects of the present invention.

DETAILED DESCRIPTION

Figure 1:
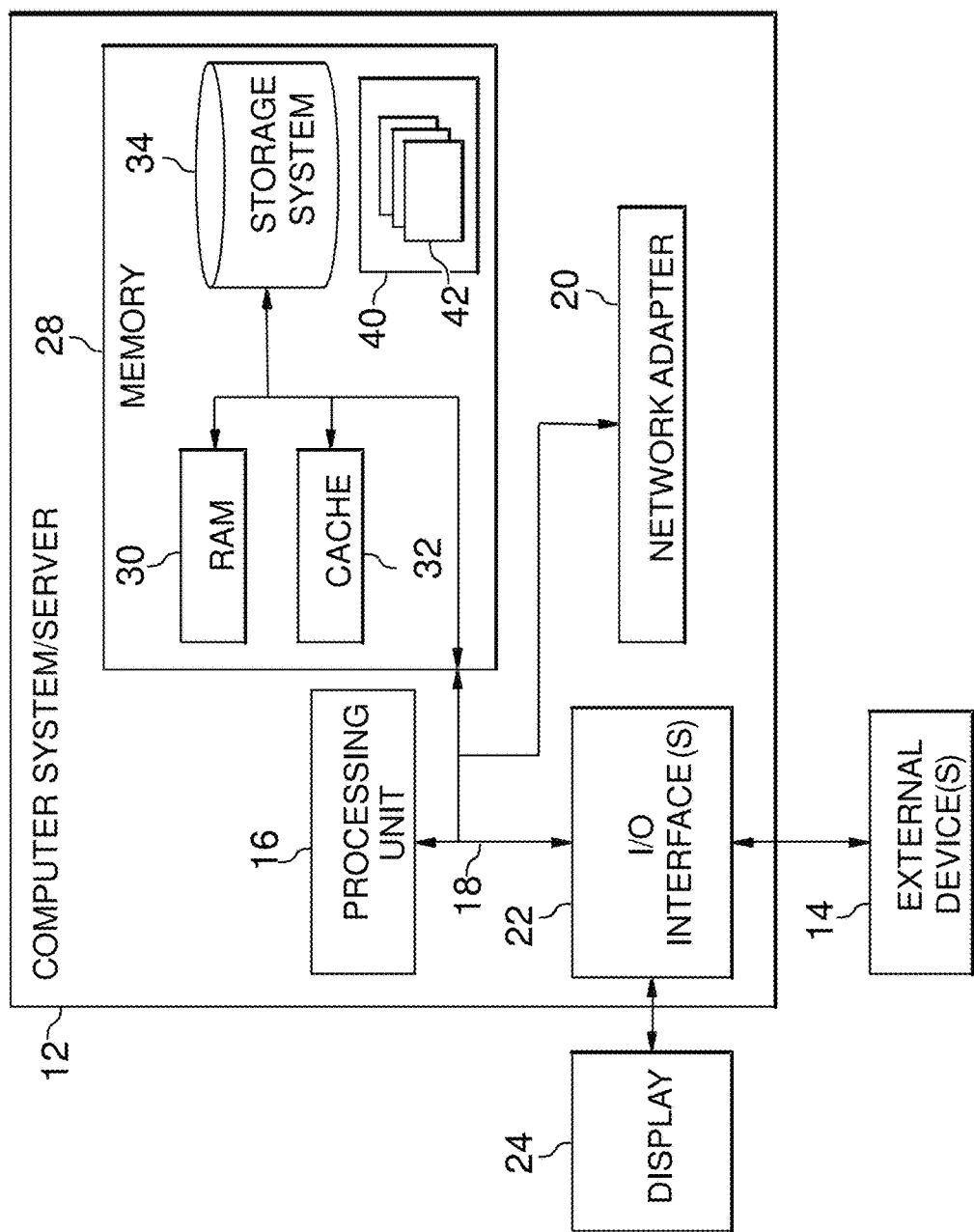
FIG. 1 depicts a cloud computing node according to an embodiment of the present invention.

The present invention generally relates to facilitating the search of individuals in a building and, more particularly, to facilitating the search of individuals in a building by controlling the operation of signaling devices to aid in the evacuation of individuals in the building during an emergency event. Aspects of the present invention may generate signaling instructions to control the operations of signaling devices within buildings such that the signaling devices aid an individual in locating an exit or responder personnel (or aid a responder to locate the individual). As an example, a search assistance server may control the operations of signaling devices, such as lights, alarms, and/or other types of devices in such a way that directs or guides an individual to an exit or responder (or a responder to an individual). In other words, controlling the operations of signaling devices may aid in the locating of individuals by a responder, or aid in the locating of a responder by an individual. Additionally, or alternatively, the search assistance server may output signaling instructions to control the operations of a user device (e.g., a smart phone, tablet, or the like) to direct or guide an individual to an exit or responder (or vice versa). In embodiments, the search assistance server may take into account power consumption and battery levels of user devices when generating signaling instructions. For example, the signaling instructions may control a user device in a way that does not over consume battery power on the user device when the user device battery level is relatively low. The search assistance server may determine the amount of power consumed by certain signaling instructions, and may control a user device for signaling purposes based on the power levels remaining on the battery of the user device so as to not drain the battery too quickly.

As described herein, the search assistance server may control the operations of signaling devices and/or user devices for guiding/locating purposes based on a location of the individual, the location of an exit/responder, the layout of the building, and the location of hazards (e.g., to avoid fires, excess smoke, flooding, etc.). As an illustrative example, the search assistance server may control the operations of lights such that the lights illuminate in a manner that guides the individual to an exit/responder, or vice versa, while avoiding hazards. Further, the search assistance server may monitor the location of the individual and modify the operations of the signaling devices (e.g., lights) based on the location of the individual relative to an exit/responder. For example, as the length of the path between the individual and exit/responder decreases, the lights may change color (e.g., to green) or change blinking pattern (e.g., slow pulsing) whereas as the length of the path between the individual and exit/responder increases, the lights may change to a different color (e.g., red) or blinking pattern (rapid blinking). Similarly, the operations of other signaling devices (e.g., alarms, sirens, audio device), etc. may be modified based on the length of the path between the individual relative to an exit/responder. For example, alarms may sound with higher or lower volumes and with different tones based depending on whether the length of the path between the individual and exit/responder is increasing or decreasing. Additionally, or alternatively, speech may be outputted with spoken commands, such as dynamic directions guiding the individual to an exit/responder or vice versa. The speech may also include a message, such as "help is on the way", distance and time to target (e.g., individual to exit/responder, or vice versa), name/description of individuals to be rescued, etc.

As further described herein, the search assistance server may control the operations of signaling devices based on triage data (e.g., health, biometrics, and/or other status information) associated with individuals located in the building. For example, the search assistance server may control the signaling devices to output different sound tones, sound patterns, speech, volumes, light colors, light patterns, etc. based on individual triage data (e.g., louder and/or more vibrant sounds and light patterns may be outputted to call more attention to those individuals in relatively poor health or may be currently incapacitated). In embodiments, search priorities may be determined based on the triage data. As an example, individuals that are in relatively poorer health, currently unconscious, or may otherwise need greater assistance may be prioritized higher for rescue operations.

As a result of the operations performed by the search assistance server, rescue operations of individuals within a building may be improved by guiding the individual to an exit or responder, or by guiding a responder to an individual. Further, triage/health data may be used to prioritize the recovery of individuals in greater need of assistance, and to better prepare responders for aiding individuals based on health conditions.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
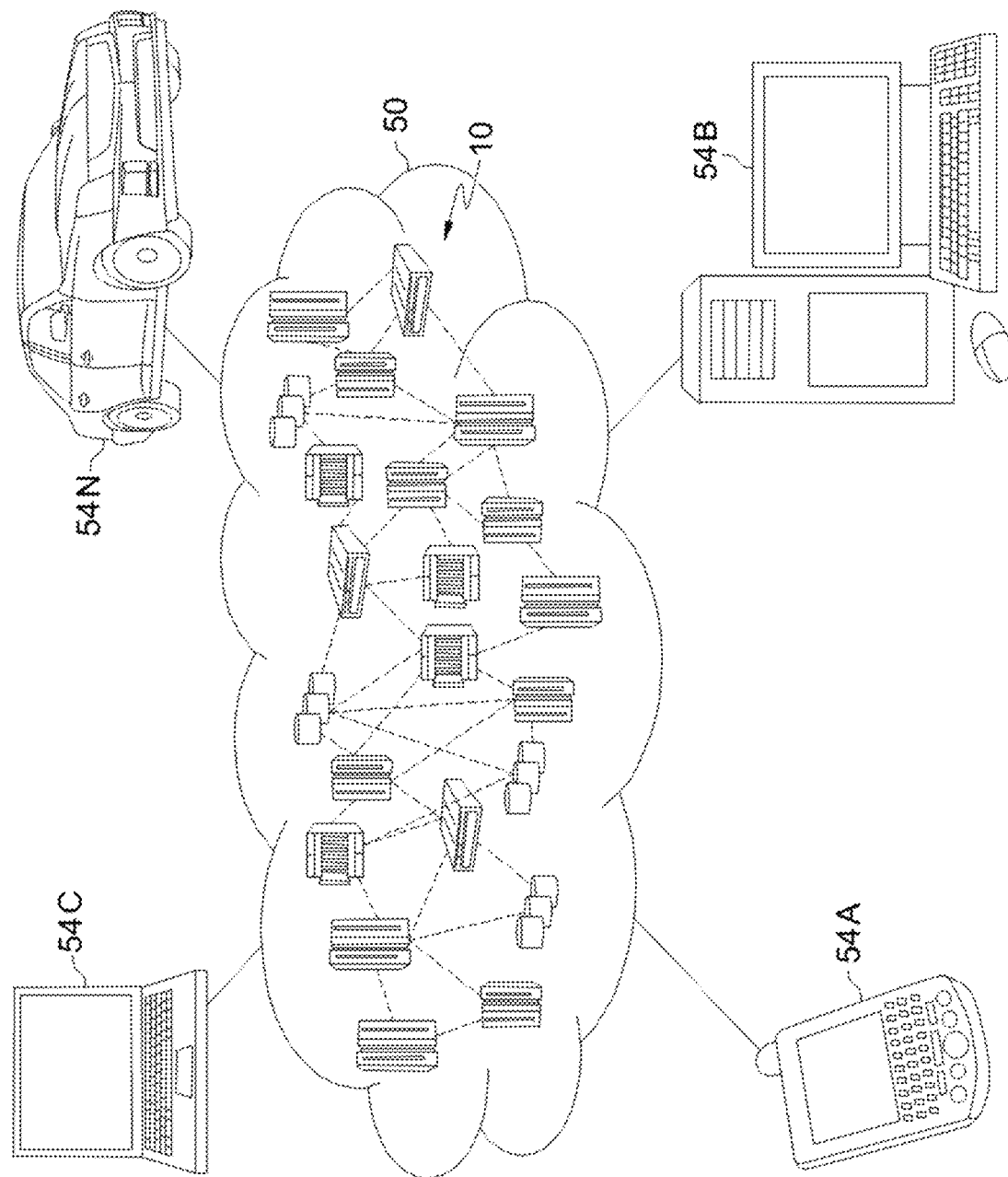
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
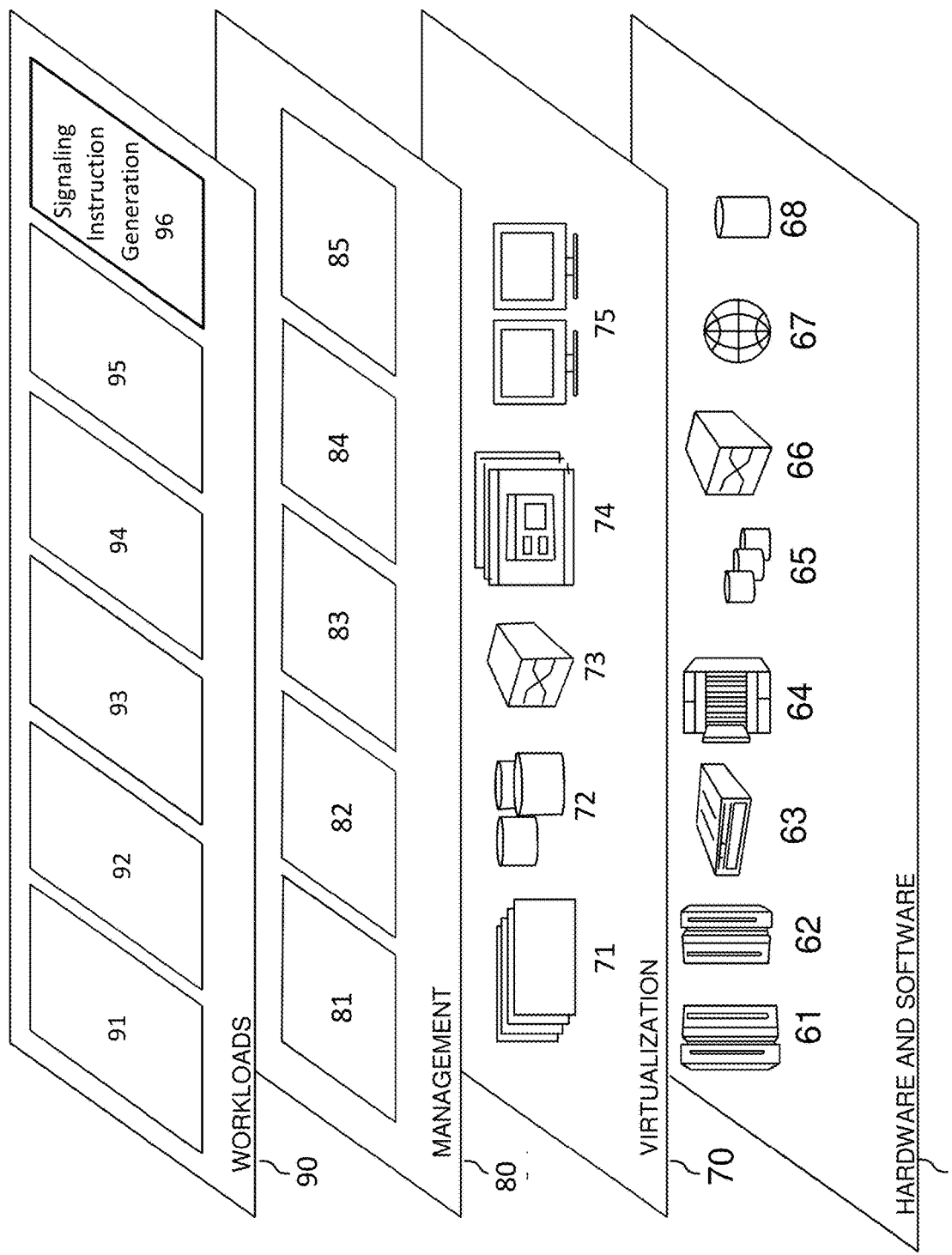
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and signaling instruction generation 96.

Referring back to FIG. 1, the program/utility 40 may include one or more program modules 42 that generally carry out the functions and/or methodologies of embodiments of the invention as described herein (e.g., such as the functionality provided by signaling instruction generation 96). Specifically, the program modules 42 may monitor and store building and individual sensor and location data, detect an emergency event within a building, identify a path between the individual and an exit or responder, determine signaling instructions based on a location of the individual, location of the exit or responder, triage information, building analytics, and/or the path, and output signaling instructions to guide an individual and/or responder as part of a rescue operation. Other functionalities of the program modules 42 are described further herein such that the program modules 42 are not limited to the functions described above. Moreover, it is noted that some of the modules 42 can be implemented within the infrastructure shown in FIGS. 1-3. For example, the modules 42 may be implemented by a search assistance server 225 as shown in FIGS. 4A and 4B.

Figure 4A:
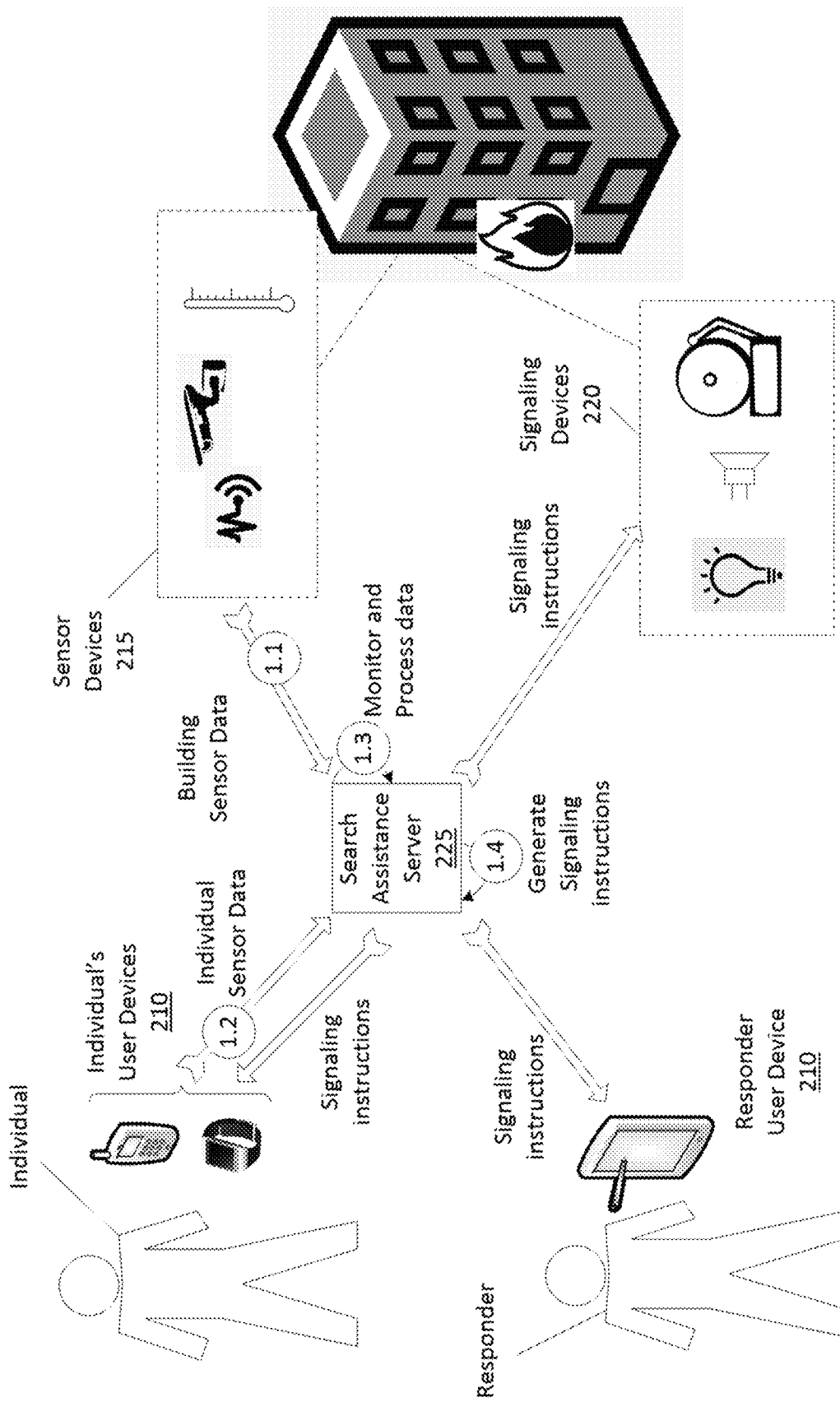
FIGS. 4A and 4B show an overview of an example implementation in accordance with aspects of the present invention.
Figure 4B:
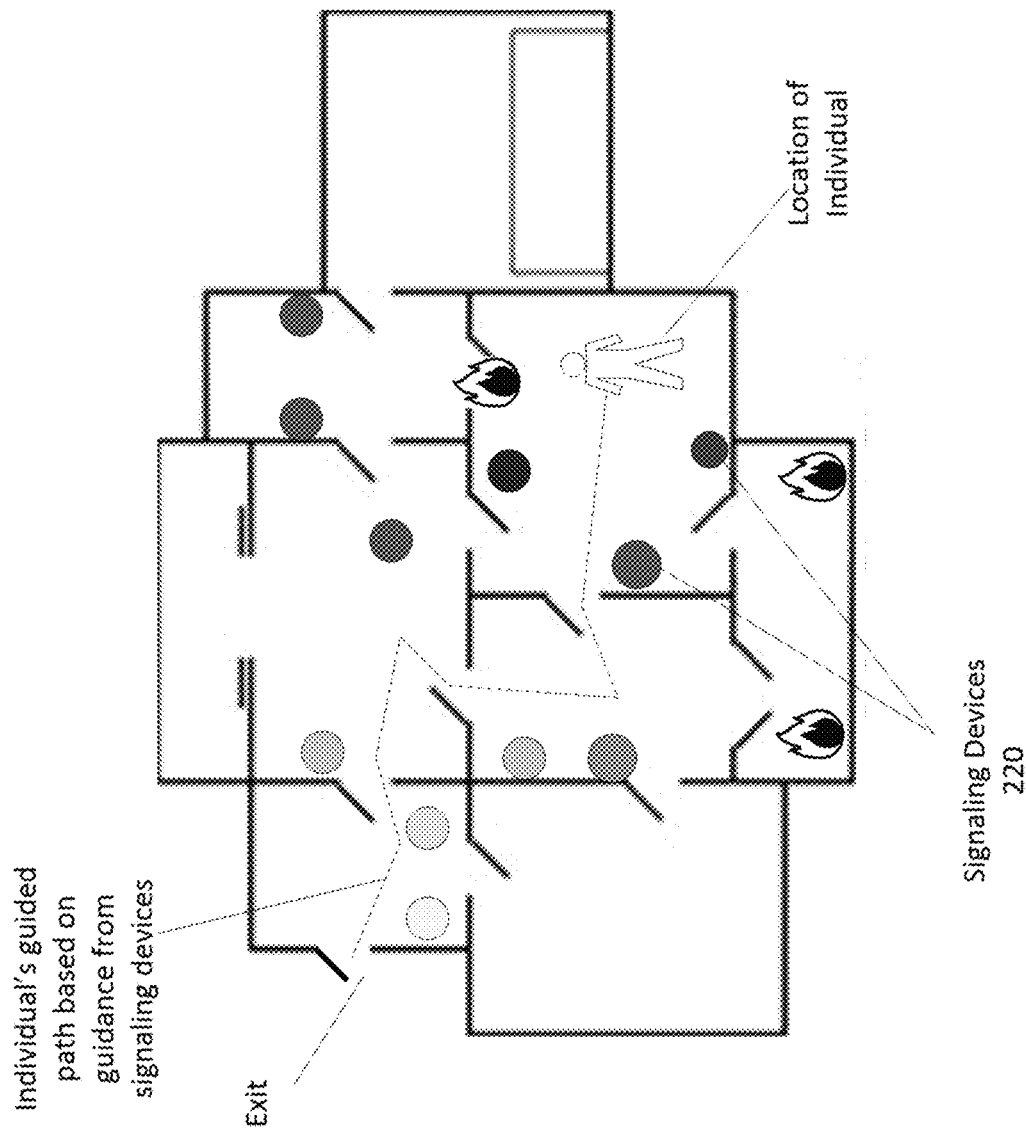

FIGS. 4A and 4B show an overview of an example implementation in accordance with aspects of the present invention. As shown in FIG. 4A, a building may include a group of sensor devices 215, such as temperature sensors, cameras, motion sensors, heat sensors, fluid sensors, smoke sensors, noise sensors, object detection sensors, location determination devices, radio signal detection devices, or the like. The building may also include a group of signaling devices 220, such as lights, speakers/audio systems, alarms, electronic displays, etc. As further shown in FIG. 4A, an individual in the building may possess one more user devices 210 (e.g., smart phones, smart watches, or the like). As shown in steps 1.1 and 1.2, a search assistance server 225 may receive building sensor data and individual sensor data. As described herein, the building sensor data may include data captured and reported by the building sensor devices 215, and the individual sensor data may include data captured and reported by the individual's user devices 210 (e.g., heart rate, body temperature, activity level, consciousness status, geographic location, or the like).

At step 1.3, the search assistance server 225 may monitor and process the building sensor data and the individual sensor data. The search assistance server 225 may detect the occurrence of an emergency event (e.g., a building fire) based on the building sensor data indicating the presence of a fire. Based on detecting the occurrence of the emergency event, the search assistance server 225 may generate signaling instructions (at step 1.4). As described herein, the signaling instructions may control the operations of signaling devices 220 and/or user devices 210 to direct or guide an individual to an exit or responder (or a responder to an individual). The search assistance server 225 may provide the signaling instructions to the signaling devices 220, user devices 210 associated with the individual, and/or user devices 210 associated with a responder. In response to receiving the signaling instructions, the signaling devices 220 and the user devices 210 may execute the signaling instructions in such a way that guides the individual to an exit or the responder (or vice versa). As an example, the signaling instructions may instruct the signaling devices 220 to illuminate lights at a certain intensity or color, output sounds at various volumes and tones, speech/spoken words, etc. Also, the signaling instructions may be displayed on the user devices 210 in the form of a map with a current location and a path from the individual to an exit or responder (or path from the responder to the individual). The signaling instructions may also direct the user device 210 to present content and/or output audio based on the proximity of the individual to the exit or responder (or vice versa).

As described herein, the search assistance server 225 may generate the signaling instructions based on a path between the individual and responder or exit. The search assistance server 225 may determine the path based on a floor layout of the building and building sensor data identifying blocked paths (e.g., paths that may not be passable due to a hazard, such as fire, flooding, excess smoke etc.). The search assistance server 225 may determine the path further based on the location of the individual and the location of an unobstructed exit and/or the responder. As described herein, the search assistance server 225 may determine the location of the individual based on Global Positioning System (GPS) information received from the individual's user device 210. Additionally, or alternatively, the search assistance server 225 may determine the location of the individual based on the strength of radio signals emitted by the individual's user device 210, communication with one or more beacons or other location determination devices implemented with the building, motion sensor data, object detection sensor data, heat detection sensor data, and/or other location determination technique.

In embodiments, the search assistance server 225 may monitor the location of the individual relative to the exit and/or responder, and may update the signaling instructions accordingly. For example, as the length of the path between the individual and exit/responder decreases, the lights may change color (e.g., to green) or change blinking pattern (e.g., slow pulsing) whereas as the length of the path between the individual and exit/responder increases, the lights may change to a different color (e.g., red) or blinking pattern (rapid blinking). Similarly, the operations of other signaling devices 220 (e.g., alarms, sirens, audio device), etc. may be modified based on the length of the path between the individual relative to an exit/responder. For example, alarms may sound with higher or lower volumes and with different tones based depending on whether the length of the path between the individual and exit/responder is increasing or decreasing. Additionally, or alternatively, speech may be outputted with spoken commands, such as dynamic directions guiding the individual to an exit/responder or vice versa. The speech may also include a message, such as "help is on the way", distance and time to target (e.g., individual to exit/responder, or vice versa), name/description of individuals to be rescued, etc. Further, signaling instructions on the user devices 210 may be modified to output different audio and/or displayed content based on the length of the path between the individual relative to an exit/responder. In this way, an individual may more easily and safely evacuate a building during an emergency situation by following the guidance of the signaling devices 220 and user device 210 that execute signaling instructions. Similarly, a responder may more easily locate an individual during an evacuation procedure.

As an example, referring to FIG. 4B, signaling devices 220 may be controlled (e.g., by the search assistance server 225) in a way that guides the user to an exit based on the presence of obstacles and blocked paths (e.g., caused by fires). In the example shown in FIG. 4B, signaling devices 220 may be lights that illuminate in a manner that guides the user to an exit. For example, the lights may be relatively darker when the user is close to a hazard or obstacle (e.g., fire). The lights may transition to a relatively lighter shade further away from the hazard and closer to the exit. It is noted that the illustration of FIG. 4B shows an example implementation of aspects of the present invention, and other examples and implementations are possible.

As described herein, signaling instructions may be based on individual sensor data, building sensor data, or directory information representing health or triage data or distress level (e.g., the individual's heart rate, consciousness, age, known health conditions, speech currently being spoken or shouted by the individual, etc.). In particular, the search assistance server 225 may take into consideration health, triage, and/or distress level data such that the signaling instructions prioritize the recovery of individuals that are in relatively poorer health, currently unconscious, have known health conditions, are in greater distress, or may otherwise need greater assistance. In embodiments, the search assistance server 225 may also prioritize the recovery of individuals based on a danger level of the individual's location within the building, or the proximity of the individual to hazards (e.g., individuals that are relatively close to a hazard and are less likely to be able to evacuate on their own may be prioritized higher).

Figure 5:
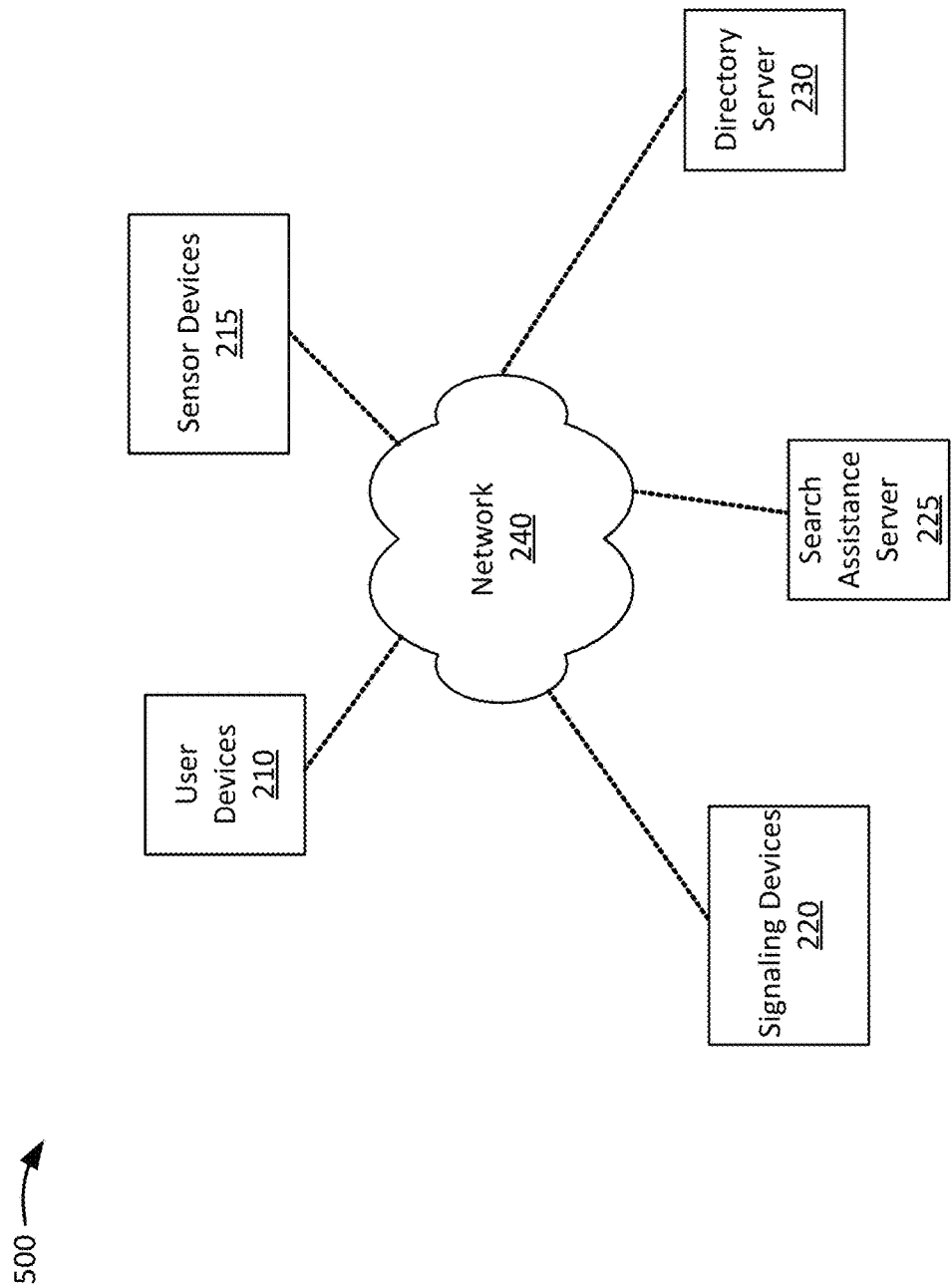
FIG. 5 shows an example environment in accordance with aspects of the present invention.

FIG. 5 shows an example environment in accordance with aspects of the present invention. As shown in FIG. 5, environment 500 may include user device 210, sensor devices 215, signaling devices 220, a search assistance server 225, a directory server 230, and a network 240. In embodiments, one or more components in environment 500 may correspond to one or more components in the cloud computing environment of FIG. 2. In embodiments, one or more components in environment 500 may include the components of computer system/server 12 of FIG. 1.

The user device 210 may include a computing device capable of communicating via a network, such as the network 240. For example, the user device 210 may correspond to a mobile communication device (e.g., a smart phone or a personal digital assistant (PDA)), a portable computer device (e.g., a laptop or a tablet computer), or another type of device. In embodiments, the user device 210 may correspond to a wearable computing device (e.g., a smart watch, smart glasses, smart clothing, etc.). In some embodiments, the user device 210 may provide biometrics and/or other health/triage data to the search assistance server 225 (e.g., heart rate, body temperature, activity level, consciousness status, etc.). Additionally, or alternatively, the user device 210 may provide location data to the search assistance server 225. The user device 210 may also receive signaling instructions from the search assistance server 225 to guide an individual to an exit or responder (or vice versa).

The sensor devices 215 may include one or more temperature sensors, cameras, motion sensors, heat sensors, fluid sensors, smoke sensors, noise sensors, object detection sensors, location determination devices, radio signal detection devices, or the like. The sensor devices 215 may be implemented within a building and may report data that the search assistance server 225 may use to detect the occurrence of an emergency event, determine safe paths between an individual and an exit or responder, and determine the presence and status of an individual. In embodiments, the sensor devices 215 may include location detection devices, such as beacons or network devices that may be used to determine specific locations of individual user devices 210.

The signaling devices 220 may include one or more lights, speakers/audio systems, alarms, electronic displays, or the like. The signaling devices 220 may receive and execute signaling instructions received from the search assistance server 225 (e.g., instructions to output light at a certain color/blinking pattern, output audio and alarms at a certain volume or tone, spoken words, etc.).

The search assistance server 225 may include one or more computing devices (e.g., such as computer system/server 12 of FIG. 1) that monitors and stores sensor data, location data, and/or other data relevant to aiding in the evacuation of individual in a building during an emergency event. As described herein, the search assistance server 225 may monitor, store, and process data for generating signaling instructions that aid in the recovery and evacuation of individuals in a building during an emergency event. In embodiments, the search assistance server 225 may monitor and store the data in a data structure in which each entry of the data structure identifies an individual, a location of the individual, building attributes at the location of the individual, sensor readings at the location of the individual (e.g., light levels, temperature, noise levels, objects, etc.), triage/health data, path between the individual and an exit, etc. When an emergency event is detected, additional data may be stored in the data structure (e.g., path to a nearest responder, signaling pattern instructions for signaling devices 220 near the user, etc.). Additional details regarding the data structure are described below with respect to FIG. 7.

The directory server 230 may include one or more computing devices (e.g., such as computer system/server 12 of FIG. 1) that stores building layout information and/or other building information used by the search assistance server 225 to determine an exit path and signaling instructions. In embodiments, the directory server 230 may store health information for an individual that may be shared with the search assistance server 225 when the individual permits sharing of health information. As described herein, health information may be used to generate signaling instructions to prioritize certain individuals based on health conditions. Also, the health information may be shared with user devices 210 of responders so that the responders may be better prepared to treat an individual upon recovery of the individual.

The network 240 may include network nodes, such as network nodes 10 of FIG. 2. Additionally, or alternatively, the network 240 may include one or more wired and/or wireless networks. For example, the network 240 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network 240 may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks.

The quantity of devices and/or networks in the environment 500 is not limited to what is shown in FIG. 5. In practice, the environment 500 may include additional devices and/or networks; fewer devices and/or networks; different devices and/or networks; or differently arranged devices and/or networks than illustrated in FIG. 5. Also, in some implementations, one or more of the devices of the environment 500 may perform one or more functions described as being performed by another one or more of the devices of the environment 500. Devices of the environment 500 may interconnect via wired connections, wireless connections, or a combination of wired and wireless connections.

FIG. 6 shows a block diagram of example components of a search assistance server in accordance with aspects of the present invention. As shown in FIG. 6, the search assistance server 225 may include a sensor data monitoring module 610, an individual data determination module 620, an individual data repository 630, an emergency or search event detection module 640, a path determination module 650, and a signaling instruction determination module 660. In embodiments, the search assistance server 225 may include additional or fewer components than those shown in FIG. 6. In embodiments, separate components may be integrated into a single computing component or module. Additionally, or alternatively, a single component may be implemented as multiple computing components or modules.

The sensor data monitoring module 610 may include a program module (e.g., program module 42 of FIG. 1) that monitors and stores sensor data received from the sensor devices 215 and from the user device 210. For example, the sensor data monitoring module 610 may monitor and store building sensor data (e.g., from data reported by the sensor devices 215 implemented within a building) and individual sensor data (e.g., from data reported by data reported by user device 210 associated with an individual within the building).

The individual data determination module 620 may include a program module (e.g., program module 42 of FIG. 1) that determines data regarding an individual present in the building. In particular, the individual data determination module 620 may identify the presence of the individual based on communications with the individual's user device 210. Additionally, or alternatively, the individual data determination module 620 may identify the presence of the individual based on heat detection, objection detection, image analysis, or the like.

The individual data determination module 620 may determine the location of the individual (e.g., based on GPS data from the individual's user device 210, strength of radio signals emitted from the individual's user device 210, communication with beacons located with the building, detection of the individual by a sensor device 215 of which the location of the sensor device 215 is known, etc.). Additionally, or alternatively, the individual data determination module 620 may determine signaling devices at the location of the individual, building elements at the location of the individual (e.g., stairs, hallways, rooms, etc.), building sensor readings at the location of the individual (e.g., light levels, temperature, noise levels, objects, etc.), or the like. Additionally, or alternatively, the individual data determination module 620 may determine triage/health data for the individual (e.g., based on sensor/biometrics data from the individual's user device 210). Additionally, or alternatively, the individual data determination module 620 may determine health conditions by accessing health records stored by the directory server 230 and shared by the individual. Additionally, or alternatively, the individual data determination module 620 may determine consciousness status of the individual (e.g., sensor/biometrics data from the individual's user device 210, image analysis indicating the consciousness status of the individual). Additionally, or alternatively, the individual data determination module 620 may determine a path between the individual and an exit (e.g., based on a layout of the building, obtained from the directory server 230, identifying the location of the exit). In embodiments, the individual data determination module 620 may determine consciousness of the individual.

The individual data repository 630 may include a data storage device (e.g., storage system 34 of FIG. 1) that stores a data structure having data for one or more individuals as determined by the individual data determination module 620. For example, for each individual, the individual data repository 630 may store the location of the individual, building attributes at the location of the individual, sensor readings at the location of the individual (e.g., light levels, temperature, noise levels, objects, etc.), triage/health data, path between the individual and an exit, path to a nearest responder, signaling pattern instructions for signaling devices 220 near the user, etc. An example of the data structure is described with respect to FIG. 7.

The emergency or search event detection module 640 may include a program module (e.g., program module 42 of FIG. 1) that detects an emergency or search event in which individuals in a building may benefit from guidance for locating an exit or responder, or an event in which responders may need to search for individuals. In embodiments, the emergency or search event detection module may detect an emergency event based on sensor data received and monitored by the sensor data monitoring module 610. As an example, the emergency or search event detection module may detect an emergency event based on smoke and/or temperature levels indicating a fire, fluid levels indicating a flood, hazardous gas levels indicating a gas leak, or the like. Additionally, or alternatively, the emergency or search event detection module may detect an emergency or search event based on detecting the toggling of an alarm (e.g., fire alarm, fire sprinklers, and/or other emergency alarm).

The path determination module 650 may include a program module (e.g., program module 42 of FIG. 1) that determines a path between the individual and an exit or responder (or a path between the responder and the individual so that the responder may search for the individual). In embodiments, the path may be determined based on the presence of hazards. For example, the path determination module 650 may detect the presence of hazards within the building (e.g., a location of a building emergency) based on the building sensor data captured and monitored by the sensor data monitoring module 610. Additionally, or alternatively, the path determination module 650 may detect the presence of hazards and/or detect path obstructions within the building via real-time video object detection from video captured by camera devices within the building supplemented by video captured by user devices 210 of the individual and/or responder. Further, the path determination module 650 may monitor obstructions and/or hazards and update the path based on the presence of new obstructions/hazards (e.g., a wall collapsing or other new obstacle that would block a previously identified path). In this way, the path determination module 650 may identify a path that avoids the detected hazards, and may identify new paths as prior paths become unpassable from new hazards/obstructions. In embodiments, the individual data repository 630 may store information identifying the path between the individual and a responder.

The signaling instruction determination module 660 may include a program module (e.g., program module 42 of FIG. 1) that generates signaling instructions based on the information stored by the individual data repository 630. In particular, the signaling instruction determination module 660 may generate signaling instructions based on the determined path (as determined by the path determination module 650), and the signaling devices near the location of the individual. As described herein, the signaling instruction determination module 660 may generate signaling instructions to control the operations of the signaling devices 220 in order to guide the individual to an exit or responder, to aid a responder in searching for the individual update the signaling instructions as the location of the individual. As described herein, the signaling instructions may also be provided to user devices 210 (e.g., the individual's user device 210 and/or a user device 210 associated with the responder) to guide the individual and/or responder. In embodiments, the signaling instruction determination module 660 may update the signaling instructions in real-time based on the travel distance between the individual and exit or responder (e.g., to inform the individual as to whether they are approaching or moving away from the exit or responder, or to inform the responder as to whether they are approaching or moving away from the individual). In embodiments, the signaling instruction determination module 660 may monitor the location of the individual and the responder based on the monitored sensor data received from the sensor data monitoring module 610 in order to determine the travel distance between the individual and exit or responder.

In embodiments, the signaling instruction determination module 660 may take into account power consumption and battery levels of user devices 220 when generating signaling instructions. For example, the signaling instructions may control a user device 220 in a way that does not over consume battery power on the user device 220 when the user device 220 battery level is relatively low. The search assistance server may determine the amount of power consumed by certain signaling instructions, and may control a user device 220 for signaling purposes based on the power levels remaining on the battery of the user device 220 so as to not drain the battery too quickly.

FIG. 7 shows an example data structure of data stored by the search assistance server for generating signaling instructions in accordance with aspects of the present invention. As shown in FIG. 700, each entry in the data structure 700 may store available information regarding an identified individual present in a building during an evacuation or emergency event. For each individual, the data structure 700 may store a name of the individual (e.g., as identified based on information from the individual's user device 210 and registered to the user), location of the individual (e.g., a room number, room name, GPS coordinates, etc.), and/or known health data (e.g., as identified from the directory server 230 when the individual's health information is shared by the individual). The data structure 700 may also store real-time health data (e.g., biometrics data from the individual's user device 210). In embodiments, the data structure 700 may further store sensor information for sensor data reported by the sensor devices 215 within the same vicinity as the user. For example, the data structure 700 may store sensor data, such as audio/visual/motion sensor data, temperature sensor data, smoke level data, or the like.

In embodiments, the data structure 700 may also store a status of the individual and/or an injury score of the individual, which may be derived by the search assistance server 225 based on the known health data, the real-time health data, the sensor information, and/or other information. For example, the data structure 700 may store a consciousness status that may be derived by the search assistance server 225 based on audio and/or motion sensor data indicating whether the individual is conscious. Additionally, or alternatively, the data structure 700 may store an injury score that may be derived by the search assistance server 225 based on the consciousness status the known health data, the real-time health data, the sensor information, and/or other information.

In embodiments, the data structure 700 may further store information identifying the user devices 210 associated with the individual (e.g., a device ID, an international mobile equipment identifier (IMEI), or the like). In embodiments, the data structure 700 may also store a location of the nearest responder (e.g. room name, description, GPS coordinates), a location of the nearest exit, a path to the exit (e.g., based on a location of the individual and blocked paths as determined by the search assistance server 225 and sensor data reported by the sensor devices 215), and a path to the nearest responder. Additionally, or alternatively, the data structure 700 may store information identifying signaling devices 220 that may be used for guiding the individual to an exit/responder, or to guide a responder to the individual.

As described herein, information stored by the data structure 700 may be updated based on the location of the individual relative to the responder. Information stored by the data structure 700 may be used to determine signaling instructions to generate and provided to the signaling devices 220. Also, information stored by the data structure 700 may be used to determine a rescue priority, which may, in turn, by used to determine signaling instructions.

In embodiments, data structure 700 may be stored by the search assistance server 225, and more specifically, by the individual data repository 630. Additionally, or alternatively, the data structure 700 may be stored by a different device. The format of data stored by the data structure 700 may differ than what is shown. Also, data structure 700 may store additional or less data than what is shown in the example of FIG. 7.

Figure 8A:
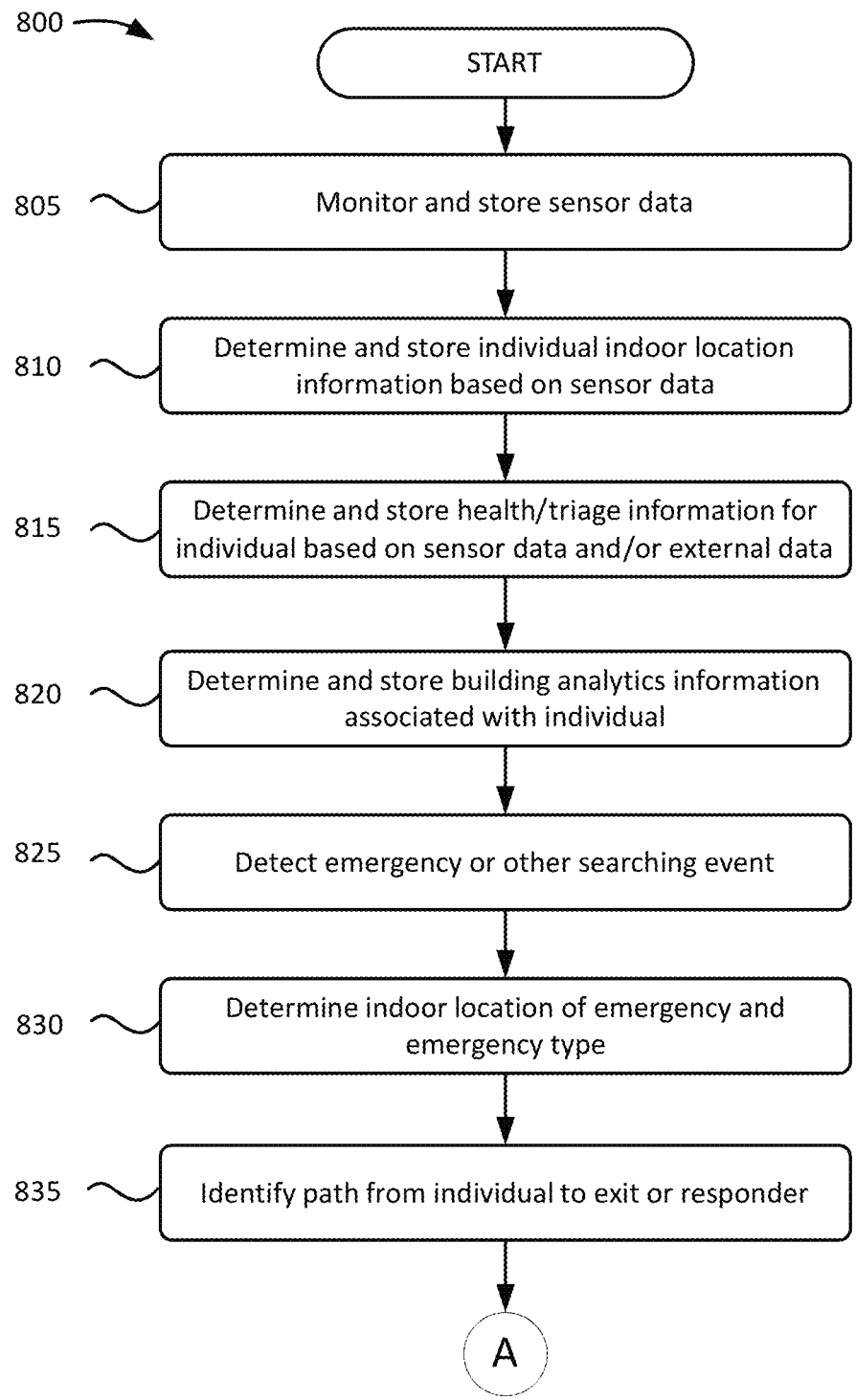
FIGS. 8A and 8B show an example flowchart of a process for controlling signaling devices for aiding in a search of an individual in a building or aiding the individual locate an exit or responder in accordance with aspects of the present invention.
Figure 8B:
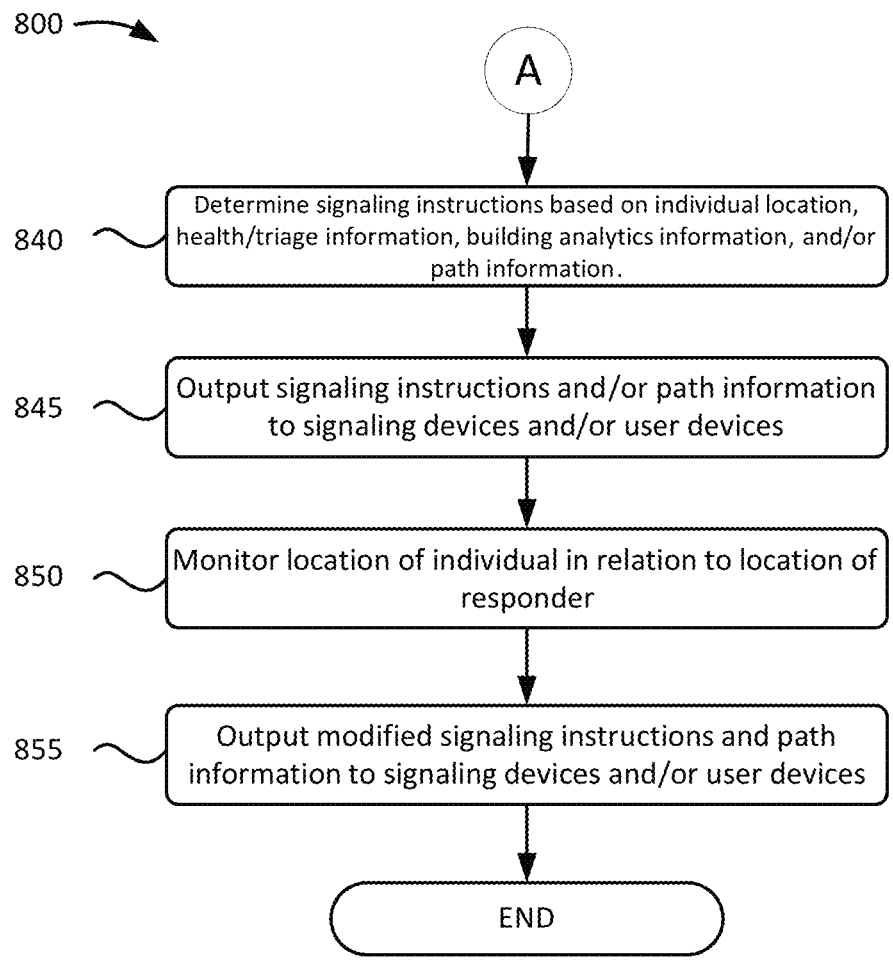

FIGS. 8A and 8B show an example flowchart of a process for controlling signaling devices for aiding in a search of an individual in a building or aiding the individual locate an exit or responder in accordance with aspects of the present invention. The steps of FIGS. 8A and 8B may be implemented in the environment of FIG. 5, for example, and are described using reference numbers of elements depicted in FIG. 5. As noted above, the flowchart illustrates the architecture, functionality, and operation of possible implementations of systems, methods, and computer program products according to various embodiments of the present invention.

As shown in FIG. 8A, process 800 may include monitoring and storing sensor data (step 805). For example, as described above with respect to the sensor data monitoring module 610, the search assistance server 225 may monitor and store building sensor data (e.g., from data reported by the sensor devices 215 implemented within a building) and individual sensor data (e.g., from data reported by data reported by user device 210 associated with an individual within the building). As described herein, search assistance server 225 may monitor and store sensor data throughout process 800.

Process 800 may also include determining and storing individual indoor location information (step 810). For example, as described above with respect to the individual data determination module 620, the search assistance server 225 may determine the location of the individual (e.g., based on GPS data from the individual's user device 210, strength of radio signals emitted from the individual's user device 210, communication with beacons located with the building, detection of the individual by a sensor device 215 of which the location of the sensor device 215 is known, etc.). Additionally, or alternatively, the search assistance server 225 may determine signaling devices at the location of the individual, building elements at the location of the individual (e.g., stairs, hallways, rooms, etc.) building sensor readings at the location of the individual (e.g., light levels, temperature, noise levels, objects, etc.), or the like. In embodiments, the individual indoor location information may be stored in a data structure, such as data structure 700.

Process 800 may further include determining and storing health/triage information for the individual based on sensor data and/or external data (step 815). For example, as described above with respect to the individual data determination module 620, the search assistance server 225 may determine triage/health data for the individual (e.g., based on sensor/biometrics data from the individual's user device 210). Additionally, or alternatively, the individual data determination module 620 may determine consciousness status of the individual (e.g., sensor/biometrics data from the individual's user device 210, image analysis indicating the consciousness status of the individual). Additionally, or alternatively, the search assistance server 225 may determine health information for the individual by accessing health records stored by the directory server 230 and shared by the individual. For example, the search assistance server 225 may identify the individual based on an identifier of the individual's user device 210, and may communicate with the directory server 230 to obtain the individual's health information. In embodiments, the health information for the individual may be stored in a data structure, such as data structure 700.

Process 800 may also include determining and storing building analytics information associated with the individual (step 820). For example, as described above with respect to the individual data determination module 620, the search assistance server 225 may determine building analytics information associated with the individual, such as signaling devices at the location of the individual, building elements at the location of the individual (e.g., stairs, hallways, rooms, etc.), building sensor readings at the location of the individual (e.g., light levels, temperature, noise levels, objects, etc.), or the like. In embodiments, the search assistance server 225 may determine the building analytics information from building plans/building layout information stored by the directory server 230. In embodiments, the building analytics information may be stored in a data structure, such as data structure 700.

Process 800 may further include detecting an emergency or search event (step 825). For example, as described above with respect to the emergency or search event detection module, the sensor device 215 may detect an emergency or search event in which individuals in a building may benefit from guidance for locating an exit or responder, or an event in which responders may need to search for individuals. In embodiments, the search assistance server 225 may detect an emergency event based on sensor data received and monitored (e.g., at step 805). As an example, the search assistance server 225 may detect an emergency event based on smoke and/or temperature levels indicating a fire, fluid levels indicating a flood, hazardous gas levels indicating a gas leak, or the like. Additionally, or alternatively, the search assistance server 225 may detect an emergency or search event based on detecting the toggling of an alarm (e.g., fire alarm or other emergency alarm).

Process 800 may also include determining indoor location of emergency and emergency type (step 830). For example, as described above with respect to the path determination module 650, the search assistance server 225 may detect the presence of hazards within the building (e.g., a location of a building emergency) based on the building sensor data captured and monitored by the sensor data monitoring module 610. As an example, the search assistance server 225 may detect the presence and location of excess smoke, fires, floods, or the like, and the location of these hazards. In embodiments, the search assistance server 225 may also determine the type of emergency (e.g., a fire emergency, a flood emergency, a seismic emergency, etc.).

Process 800 may further include identifying a path from the individual to an exit and/or responder (step 835). For example, as described above with respect to the path determination module 650, the search assistance server 225 may determine a path between the individual and an exit or responder (or a path between the responder and the individual so that the responder may search for the individual). As described herein, the path may be based on the location of hazards such that to avoid the hazards. In embodiments, the search assistance server 225 may determine the location of exits based on building plan/layout information stored by the directory server 230. The search assistance server 225 may determine the location of a responder based on GPS coordinates from the responder's user device 210, communication between the responder's user device 210 and location determination devices, or some other location determination technique. While a responder may use a user device 210 to aid in locating an individual, it is noted that use of a user device 210 is not necessary for locating the individual. For example, the responder may use the guidance from the signaling devices 220 to locate the individual without the need for a user device 210.

Referring to FIG. 8B, process 800 may also include determining signaling instructions based on individual location information, health/triage information, building analytics information, and/or path information (step 840). For example, as described above with respect to the signaling instruction determination module 660, the search assistance server 225 may generate signaling instructions based on the information stored by the individual data repository 630 (e.g., including information such as the individual location information, health/triage information, building analytics information, and/or path information). In particular, the search assistance server 225 may generate signaling instructions based on the determined path (as determined by the path determination module 650), and the signaling devices 215 near the location of the individual. As described herein, the search assistance server 225 may generate signaling instructions to control the operations of the signaling devices 220 in order to guide the individual to an exit or responder, to aid a responder in searching for the individual update the signaling instructions as the location of the individual. As described herein, the signaling instructions may also be provided to user devices 210 (e.g., the individual's user device 210 and/or a user device 210 associated with the responder) to guide the individual and/or responder. Examples of signaling instructions may include instructions to direct the signaling devices 220 to output light of a certain color or blinking pattern based on the length of the path between the responder and individual, instructions to direct the signaling devices 220 to output audible alarms of certain patterns/tones, spoken words with directions, messages, etc, instructions to display location information and/or directions on the individual's and/or responder's user devices 210, etc.

Process 800 may further include outputting signaling instructions and/or path information to signaling devices and/or user devices (step 845). For example, as described above with respect to the signaling instruction determination module 660, the search assistance server 225 may output the signaling instructions and/or path information to the signaling devices 220 and/or user devices 210 (e.g., the individual's and/or the responder's user device 210). Based on receiving the instructions, the signaling devices 220 and/or the user devices 210 may execute the signaling instructions, thereby causing the signaling devices 220 and/or user devices 210 to output lights, sounds, maps, and/or other content in a manner that guides the individual to the responder or exit, and/or guiding the responder to the individual.

Process 800 may also include monitoring the location of the individual in relation to the location of the responder (step 850). For example, as discussed above with respect to the signaling instruction determination module 660, the search assistance server 225 may monitor the location of the individual in relation to the location of the responder (e.g., using one or more suitable location determination techniques, such as GPS tracking of user devices 210, signal strength analysis, heat analysis, object detection, etc.). The search assistance server 225 may monitor the travel distance between the user and exit/responder based on tracking the location of the individual in relation to the location of the responder or exit.

Process 800 may further include outputting modified signaling instructions and path information to signaling devices and/or user devices (step 855). For example, as discussed above with respect to the signaling instruction determination module 660, the search assistance server 225 may update the signaling instructions in real-time based on the travel distance between the individual and exit or responder (e.g., to inform the individual as to whether they are approaching or moving away from the exit or responder, or to inform the responder as to whether they are approaching or moving away from the individual). As an example, the search assistance server 225 may update the signaling instructions to direct signaling devices 220 to alter their operations in such a way that guides the individual to an exit or responder, or a responder to the individual (e.g., by modifying the color/intensity of lighting, tone/volume of sound, spoken words such as dynamic directions, messages, or individual's information, displayed content on an electronic display, etc.).

As a result of the operations performed by the search assistance server 225, rescue operations of individuals within a building may be improved by guiding the individual to an exit or responder, or by guiding a responder to an individual. Further, triage/health data may be used to prioritize the recovery of individuals in greater need of assistance, and to better prepare responders for aiding individuals based on health conditions.

In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system/server 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   determining, by a computing device, a location of an individual in a building relative to the location of an exit of the building;
   determining, by the computing device, locations of obstacles or hazards within the building;
   determining, by the computing device, distress level data representing a distress level associated with the individual;
   determining, by the computing device, a path from the individual to the exit based on determining the location of the individual relative to the exit and the locations of the obstacles or hazards;
   selecting, by the computing device, a type of signaling instructions based on the path and the distress level data; and
   generating, by the computing device, signaling instructions of the selected type of signaling instructions based on the path and the distress level data.

2. The method of claim 1, further comprising:
   monitoring, by the computing device, the location of the individual relative to the location of the exit of the building; and
   updating, by the computing device, the signaling instructions based on the monitoring the location of the individual.

3. The method of claim 1, wherein the signaling instructions control at least one operation of the signaling devices selected from the group consisting of:
   light color;
   audio output rate;
   audio output tone;
   audio output speech or spoken words;
   audio output speech; and
   displayed content.

4. The method of claim, 1 wherein the one or more signaling devices include at least one from the group consisting of:
   lighting devices;
   audio output devices; and
   electronic display devices.

5. The method of claim 1, wherein the location of the individual is determined based on at least one selected from the group consisting of:
   signal strength analysis from signals emitted by the user device of the individual;
   object detection sensor data;
   heat sensor data;
   audio sensor data; and
   visual camera data.

6. The method of claim 1, wherein the location of the obstacles is determined based on object detection sensor data.

7. The method of claim 1, further comprising determining, by the computing device, a path from the individual to a responder, wherein the generating the signaling instructions is further based on the path between the individual to the responder.

8. The method of claim 1, further comprising:
   determining respective locations of a plurality of different individuals; and
   generating respective signaling instructions for each of the plurality of different individuals based on the respective locations.

9. The method of claim 8, further comprising: determining, by the computing device, distress level data that indicates a distress level associated with each of the plurality of different individuals, wherein the generating the signaling instructions is further based on the distress level data of the plurality of different individuals.

10. The method of claim 9, further comprising determining, by the computing device, a rescue priority based on the distress level data of the plurality of individuals, wherein the generating the signaling instructions is further based on the rescue priority.

11. The method of claim 1, further comprising detecting, by the computing device, an emergency event based on sensor data reported by one or more sensor devices, wherein the generating the signaling instructions is based on detecting the emergency event.

12. The method of claim 1, wherein a service provider at least one of creates, maintains, deploys and supports the computing device.

13. The method of claim 1, wherein the computing device includes software provided as a service in a cloud environment.

14. A computer program product for assisting with rescue operations during a building emergency, the computer program product comprising a computer readable storage medium having program instructions embodied therewith, the program instructions executable by a computing device to cause the computing device to:
   determine a location of an individual in a building relative to the location of a responder;
   determine locations of obstacles or hazards within the building;
   determine distress level data representing a distress level associated with the individual;
   determine a path from the individual to the responder based on determining the location of the individual relative to the responder and the locations of the obstacles or hazards;
   select a type of signaling instructions based on the path and the distress level data; and
   generate signaling instructions of the selected type of signaling instructions based the path and the distress level data.

15. The computer program product of claim 14, wherein the program instructions further cause the computing device to:
   monitor the location of individual relative to the location of the responder;
   monitor the location of the obstacles or hazards; and
   update the signaling instructions based on the monitoring the location of the individual and the location of the obstacles or hazards.

16. The computer program product of claim 14, wherein the program instructions further cause the computing device to:
   determine respective locations of a plurality of different individuals; and generate respective signaling instructions for each of the plurality of different individuals based on the respective locations.

17. The computer program product of claim 16, wherein the program instructions further cause the computing device to determine distress level data representing a distress level associated with each of the plurality of different individuals, wherein the generating the signaling instructions is further based on the distress level data of the plurality of different individuals.

18. The computer program product of claim 17, wherein the program instructions further cause the computing device to determine a rescue priority based on the distress level data of the plurality of individuals, wherein the generating the signaling instructions is further based on the rescue priority.

19. A system comprising:
- a CPU, a computer readable memory and a computer readable storage medium associated with a computing device;
- program instructions to determine a location of an individual in a building relative to the location of a responder or relative to a location of an exit of the building;
- program instructions to determine locations of obstacles or hazards within the building;
- program, instructions to determine distress level data representing a distress level associated with the individual;
- program instructions to determine a path from the individual to the responder or a path from the individual to the exit based on determining the location of the individual and the location of the obstacles or hazards;
- program instructions to select a type of signaling instructions based on the path and the distress level data; and
- program instructions to generate signaling instructions of the selected type of signaling instructions based on the path and the distress level data, wherein the program instructions are stored on the computer readable storage medium for execution by the CPU via the computer readable memory.

20. The system of claim 19, further comprising:
- program instructions to output the signaling instructions to one or more signaling devices, wherein the outputting the signaling instructions controls operations of the one or more signaling devices to guide the individual to the responder, the responder to the individual, or the individual to the exit based on the path;
- program instructions to monitor the location of the individual or responder;
- program instructions to update the signaling instructions based on the monitoring the location of the individual or responder; and
- program instructions to output the updated signaling instructions to the one or more signaling devices.

* * * * *